United States Patent [19]

Marcinkowsky et al.

[11] 4,174,353
[45] Nov. 13, 1979

[54] OLEFIN SEPARATION PROCESS

[75] Inventors: Arthur E. Marcinkowsky, Charleston; George E. Keller, II, South Charleston; Surendra K. Verma, Charleston, all of W. Va.

[73] Assignee: Union Carbide Corporation, New York, N.Y.

[21] Appl. No.: 919,420

[22] Filed: Jun. 27, 1978

[51] Int. Cl.$^2$ ............................................. C07C 7/01
[52] U.S. Cl. ................................. 585/835; 585/838; 585/839; 585/844
[58] Field of Search ................................. 260/677 A

[56] References Cited
U.S. PATENT DOCUMENTS

| | | | |
|---|---|---|---|
| 2,831,907 | 4/1958 | Mayfield et al. | 260/669 R |
| 2,913,505 | 11/1959 | Van Raay et al. | 260/677 |
| 3,101,381 | 8/1963 | Baxter | 260/677 A |
| 3,189,658 | 6/1965 | Quinn | 260/677 A |
| 3,331,190 | 7/1967 | Glew et al. | 260/677 A |
| 3,395,192 | 7/1968 | Long | 260/677 |
| 3,402,212 | 9/1968 | Gantt | 260/669 R |

*Primary Examiner*—C. Davis
*Attorney, Agent, or Firm*—Gerald R. O'Brien, Jr.

[57] ABSTRACT

There is disclosed a process for the separation of ethylene or propylene from a purified, multi-component gas stream produced from the thermal cracking of hydrocarbons and containing ethylene or propylene and other low molecular weight components comprising the steps of: introducing said multi-component gas stream into an aqueous silver salt solution stream to effect the absorption and/or complexing of said contained ethylene or propylene and reaction of trace acetylenes with the silver metal ions of such solution; venting of the silver salt solution stream at reduced pressure to remove the dissolved other low molecular weight components; treating the resulting silver salt solution stream to separate the absorbed and/or complexed ethylene or propylene from the silver salt stream; further treating the resultant silver salt solution stream to release the contained trace acetylenes therefrom and provide an aqueous silver salt stream; and recycling said aqueous silver salt stream to said introducing step.

9 Claims, 4 Drawing Figures

OLEFIN SEPARATION PROCESS

The present invention relates to an olefin separation process and, more particularly, such a process employing complexing with metal ions.

It is known that some metal ions complex selectively with unsaturated organic compounds. Some of these complexes are reversible while others are irreversible. Aqueous silver salt in solution offers an example of a metal ion which complexes with olefins reversibly and with acetylenes irreversibly. This property of the silver ions in aqueous solution may be employed in absorbing olefins selectively out of a mixture of gases in which the other components are relatively inert toward the silver salt solution. Based on this property, a process is provided to separate ethylene or propylene from a purified multi-component gas stream produced from the thermal cracking of hydrocarbons and containing $C_2$, $C_3$ and lighter components. Following the removal of acetylene, the other gas stream components are relatively less soluble in the solution and may be treated as inerts.

In general, when a gaseous component solubilizes in a liquid and complexes with its ions, the loading of the gas is greatly affected by its partial pressure, the temperature and the concentration of the complexing ions in the solution. Therefore, by changing the physical conditions separately or collectively, the active gaseous component can either be formed into or out of the solution.

The physical parameters swing method has been employed here to carry out an ethylene or propylene separation using an aqueous nitrate solution. In order to specify the process design conditions for absorption and desorption of the gas and thereby carry out an effective separation of the active gas from the inerts, a knowledge of the vapor-liquid equilibria is very important. Experimental work has been carried out measuring the vapor-liquid equilibrium on the ethylene-silver nitrate solution and the propylene-silver nitrate solution systems in the pressure range of 0.1 to 150 psia and over a temperature range of 5° to 60° C. for 1 to 6 molar silver nitrate solution. The preferred parameter values have been selected following an analysis of the data for such work.

Although the gaseous components other than ethylene or propylene do not solubilize in solution or complex with silver ions as readily as ethylene does, a small quantity of these components absorb into the silver solution during the process of ethylene absorption. This small quantity of these inert components will desorb with the ethylene or propylene as impurities. Therefore, if the recovered ethylene or propylene is required to meet some product quality standards, it is necessary that these impurities be stripped off the solution before the ethylene or propylene is recovered. Thus, the overall process of ethylene or propylene separation by metal complexation can be divided into three major sections, namely: absorption; venting of impurities or purification; and desorption.

In accordance with the present invention, a process is provided for the separation of ethylene or propylene from a purified, multi-component gas stream produced from the thermal cracking of hydrocarbons and containing ethylene or propylene and other low molecular weight components comprising the steps of:

(a) introducing said multi-component gas stream into an aqueous silver salt solution stream to effect the absorption and/or complexing of said ethylene or propylene and reaction of trace acetylenes with the silver metal ions of such solution;

(b) venting of the silver salt solution stream at reduced pressure to remove the dissolved other low molecular weight components and a small amount of ethylene which may be subsequently compressed and recycled to the inlet feed introducing step;

(c) treating the resulting silver salt solution stream to separate the absorbed and/or complexed ethylene or propylene from the silver salt stream;

(d) further treating the resultant silver salt solution stream to release the contained trace acetylenes therefrom and provide an aqueous silver salt stream; and (e) recycling said aqueous silver salt stream to said introducing step.

Figure 1:
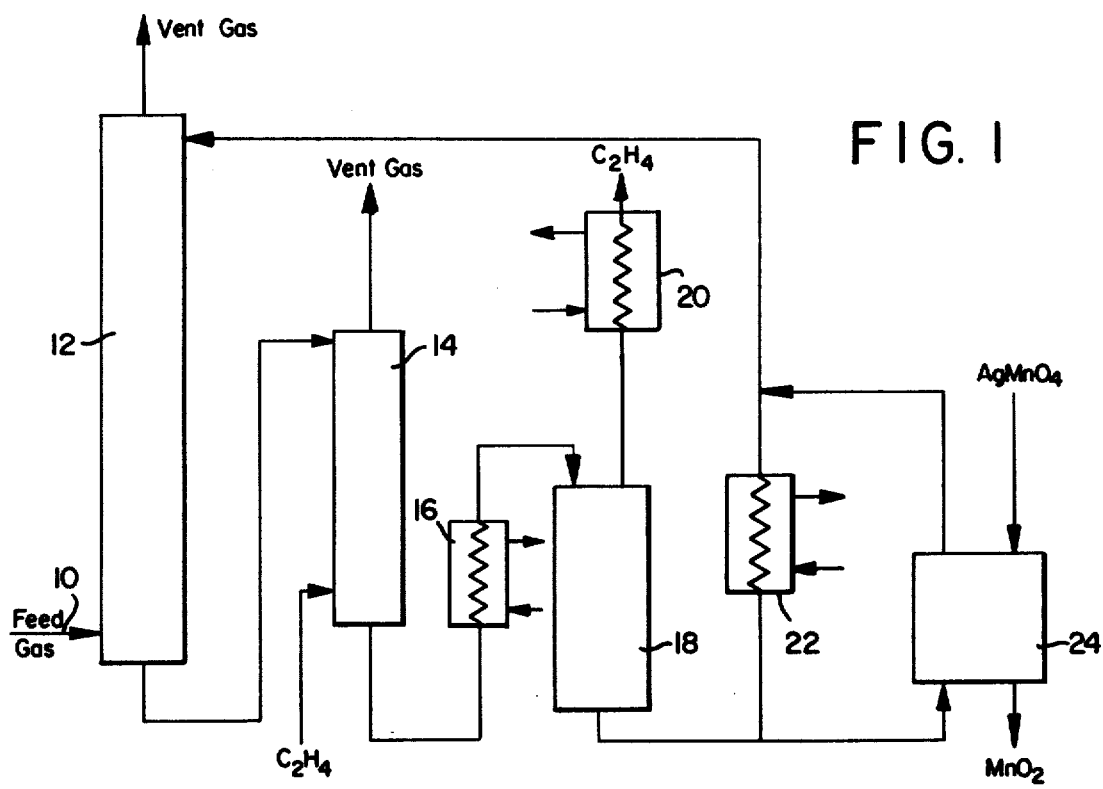
FIG. 1 is a schematic showing of a flow diagram of the process of the present invention.

As indicated schematically in the simplified process flow diagram of FIG. 1, the absorption of ethylene or propylene from the crude feed gas stream is carried out under pressure in a counter-current absorber column. Initially, the absorber column was operated at 240 psia total pressure and at temperatures ranging between 30 and 45° C. Subsequently, the pressure of the absorber column was increased to 295 psia because of the inlet conditions of the feed gas stream, available after the pretreatment.

Ethylene or propylene take-up by silver nitrate solution is an exothermic process. Part of this heat needs to be removed in order to obtain higher loading of ethylene or propylene in the solution. A possibility exists to recover this heat with a heat pump and use it in the stripper section as an energy-saving step for the process.

For ethylene, overall analysis of the process suggests that the preferred concentration of the silver nitrate solution is 3 M, a higher solution concentration favoring the heat recovery cycle and reducing the volume of the solution for the process. On the other hand, lower solution concentration reduces the silver inventory/losses and make it easier and more economical to stabilize the silver ion in the solution.

In the absorption step of the process as applied to ethylene separation, other components (CO, $H_2$, $CH_4$, $C_2H_6$, etc.) of the gaseous mixture are also physically absorbed in the solution or weakly complexed with silver ions. The function of the venting step of the process is to strip these impurities out of the solution before ethylene is recovered. The venting step is operated under a pressure (preferably about 100 psia) which is somewhat below the partial pressure of ethylene (132 psia) in the absorber step. The flashing of the solution to a lower pressure gives off a small part of the absorbed gases which may be recycled to the absorber.

In order to carry out the ethylene separation successfully, the feed gas to the absorber must be free from components which react with silver ions irreversibly or are absorbed readily in the solution. Otherwise, these constituents would either contaminate the silver solution and eventually precipitate in the columns or contaminate the separate ethylene. This requires that the feed gas stream, before entering the absorber, should be processed in order to remove the undesirable constituents either completely or to certain acceptable limiting values. The various processing through which the multicomponent thermally cracked hydrocarbon gas stream is passed, for purification, before it is ready for ethylene separation by metal complexing are summarized below.

Acid gases and acetylene are removed from the cracked gas stream prior to its treatment in the silver complexing process of the invention. An ethanolamine system may be employed to remove the acid-gases ($H_2S$ and $CO_2$) from the cracked gas stream. Acetylene reacts irreversibly with silver ions and forms silver acetylide which not only removes silver ions from the solution, but also represents a safety hazard when dry. Therefore, removal of acetylene, either completely or to a minimum permissible level, is essential.

Either of two alternative methods may be employed for removing acetylene from the gas stream before it enters the ethylene separation unit: removal with a chilled polar solvent, such as dimethyl formamide or acetone in an absorption process; or selective acetylene dehydrogenation over a noble metal catalyst. Each method is capable of reducing the acetylene to a level of about 1 ppm of the contained ethylene. This remaining acetylene complexes irreversibly with silver ions in the absorber column and forms silver acetylide.

As pointed out in FIG. 1 of the article "Ethylene From Crude Oil" by Hosoi & Keister in Chemical Engineering Progress (Vol. 71, No. 11) November 1975, page 63, the quenched ACR cracked hydrocarbon product stream is successively fractionated to remove pitches, tars and oils and treated with DEA or the like to absorb and subsequently strip carbon dioxide and hydrogen sulfide. The resulting "sweet" gas stream may then be split to remove any desired fraction.

The most commonly desired fraction is the $C_2$ split fraction containing ethylene and the other components set forth in Table I. The $C_3$ and higher components of the splitting of the sweet gas stream may be treated in the same manner, at slightly different temperatures, pressures and additive concentrations as is the $C_2$ split fraction to effect the production of propylene by separation from propane and trace amounts of butadiene, methyl-acetylene, vinyl acetylene, allene and butene. The $C_3$ split fraction will typically contain 90-96 vol. % propylene; 4-10 vol. % propane (depending on the degree of cracking in the ACR process) and the trace amounts stated above in lower parts per million concentrations. The discussions herein and examples and other data set forth, however, deal primarily with the application of the separation process of the present invention to the production of ethylene from a purified $C_2$ split fraction of ACR cracked hydrocarbon product stream.

In the production of ethylene, all the heavy components ($C_3$ and above) in the hydrocarbon cracked feed gas stream are removed at various stages of purification. However, some propylene accompanies the $C_2$ split stream, even after such purification. Since the solubility of propylene in the silver salt solution is of the same order as that of ethylene, most of the propylene passes along with the recovered ethylene. Therefore, it is preferred that the level of propylene in the purified $C_2$ split stream should be such that it meets product quality standards not exceeding 10 ppm.

The process of the invention has been analyzed on the basis of feed gases coming from the cracking furnace and having two ethylene/acetylene ratios, e.g. E/A=5 and E/A=15. Based on those two alternative degrees of cracking, the two feed gas streams available after purification (including acid gas and acetylene removal) and splitting into an ethylene ($C_2$) stream fraction, the composition was as set forth in Table I.

TABLE I

Feed Gas to Conventional or Silver Complexing Hydrogen/Methane/Ethylene Recovery Systems

| Feed E/A ratio | 5 | (mild cracking) | 15 | (heavy cracking) |
|---|---|---|---|---|
| Pressure, psia | 295 | | 295 | |
| Temperature, °C. | 2.6 | | 4.7 | |
| Rate, M lb/hr | 204.8 | | 179.1 | |
| Mol. Wt. | 16.07 | | 18.13 | |

| Component | M.F.* | M lb/hr | M.F.* | M lb/hr |
|---|---|---|---|---|
| Hydrogen | 0.3704 | 9.517 | 0.3034 | 6.042 |
| Nitrogen | 0.0033 | 1.181 | 0.0039 | 1.095 |
| Carbon Monoxide | 0.0607 | 21.654 | 0.0318 | 8.804 |
| Methane | 0.1983 | 40.538 | 0.1746 | 27.665 |
| Acetylene | 0.350 (ppm) | 0.000116 | 0.451(ppm) | 0.000116 |
| Ethylene | 0.3503 | 125.258 | 0.4520 | 125.250 |
| Ethane | 0.0160 | 6.141 | 0.0331 | 9.833 |
| Propylene | 0.0010 | 0.549 | 0.00099 | 0.409 |

*Mole Fraction

In the production of ethylene, the purified, split feed gas fraction entering the absorber carries with it approximately 0.3 ppm acetylene. This acetylene impurity reacts instantaneously and irreversibly with Ag+ to form silver acetylide. Since $Ag_2C_2$ in the dry state is a highly reactive compound, provision must be made to eliminate it from the process $AgNO_3$ solution at least to such levels that no possibility of its precipitation from a standard solution under the worst combination of conditions could occur. By knowing the solubility of silver acetylide in aqueous $AgNO_3$ solutions, maximum allowable $Ag_2C_2$ concentration limits can be safely established.

The solubility of $Ag_2C_2$ in aqueous solutions of silver nitrate over a concentration range of 25 to 65 wt. percent $AgNO_3$ was determined at 15°, 25° and 35° C. In general, the solubility increases with an increase in temperature at constant molarity and increases, at constant temperature, with an increase in $AgNO_3$ concentration. For example, at 59.27 wt. percent $AgNO_3$ (6M at 25°), the $Ag_2C_2$ solubility varies from 1.13 cc $C_2H_2$ at RTP/cc $AgNO_3$ solution at 15° C. to 3.75 cc $C_2H_2$ at RTP/cc $AgNO_3$ solution at 35° C.

It should also be noted that the presence of excess nitric acid depresses the $Ag_2C_2$ solubility. Once the most stringent conditions are set, the solubility tolerance should preferably be set at about one-half the actual value.

One of the important aspects relating to the elimination and control of $Ag_2C_2$ build-up in the extraction solution involves employing an effective analysis method which can be employed without having to isolate solid $Ag_2C_2$. The method developed and employed in connection with the present invention is based on the redox property of $KMnO_4$. Under strongly acidic conditions the $MnO_4^-$ ion is reduced to $Mn^{+2}$, whereas in essentially neutral conditions, the reduction only proceeds to $Mn^{+4}$. The former condition was selected because (i) the $Mn^{+2}$ ion is soluble versus the insolubility of $MnO_2$, which also improves the reproducibility and (ii) since the $Mn^{+2}$ solution remains essentially colorless, the $MnO_4^-$ ion also acts as its own indicator.

The stoichiometry of the reaction is as follows:

$$8H^+ + 2MnO_4^- + C_2^{--} \rightarrow 2Mn^{+2} + 4H_2O + 2CO_2$$

The method of destroying $Ag_2C_2$ which accumulates in the aqueous $AgNO_3$ extracting solution is based on the use of silver permanganate, $AgMnO_4$, as the oxidant, under essentially neutral or slightly acidic conditions so that the reduction of the $MnO_4^-$ only goes to $MnO_2$. In this method a small side-stream containing dissolved $Ag_2C_2$ is taken and (i) heated under partial vacuum to approximately 75° C. which would serve to expel any small traces of ethylene still in solution and simultaneously, thermally degrade whatever $H_2O_2$, which is added to control Ag precipitation, is still in the solution. At this point (ii), an analysis for $Ag_2C_2$ content is carried out and (iii) the necessary solid $AgMnO_4$ added to reduce the acetylide to the desired concentration. (iv) The solid $MnO_2$ formed during the reaction is filtered away and the solution with proper adjustment of acid content and makeup water, etc. is returned to the main hoop. The stoichiometry for the oxidation of the acetylide ion under essentially neutral conditions is as follows:

$$10MnO_4^- + 3C_2^{--} + 8H_2O \rightarrow 10MnO_2 + 6CO_2 + 16OH^-$$

The metathesis of $AgMnO_4$ is carried out by mixing $KMnO_4$ (0.5M) and $AgNO_3$ (3.0M) solutions, and is an integral part of the overall process. It involves recycling of about 90 percent of the filtrate from the $AgMnO_4$ metathesis to dissolve $KMnO_4$, and thereby reducing the silver loss in the effluent stream by a factor of about 25.

Shock sensitivity tests (drop-weight) were run on samples of moist slurries and dried silver acetylide adducts to determine the relative sensitivity to mechanical shock. Two samples of acetylide slurry made in a 3 molar and 8 molar $AgNO_3$ solution were drained of liquid and tested in the drop weight test. Ten trials were made on each sample at the maximum potential energy of the test (300 Kg-cm) with all trials "no-go", indicating no sensitivity to shock with these drained samples containing approximately 40–50 percent water. The 8 molar material was dried in an evacuated desiccator and twelve trials on this sample gave a sensitivity value of 225 Kg-cm. As a comparison, a slurry was made by bubbling acetylene through a very dilute $AgNO_3$ solution (0.1M) to obtain almost pure silver acetylide. Twelve trials of this dried material gave a sensitivity value of 128 Kg-cm, indicating more sensitivity than the material from the 8M solution, which probably contained the adduct $(Ag_2C_2)_n \cdot (AgNO_3)_p$.

Study indicates the inherent shock stability of the wet acetylide slurries and the danger of the dry material to shock. Generally, the purer the dry silver acetylide, the more sensitive it is to shock detonation.

The only component heavier than $C_2$ that is expected to be present in the hydrocarbon feed gas stream is propylene. Propylene behaves very similarly to ethylene and complexes with the silver ions in the solution. Therefore, most of the propylene present in the feed gas stream will stay with ethylene during the separation process. Hence, the propylene concentration should be reduced in the feed gas stream to a minimum acceptable level in ethylene. Presently, it is believed that only 10 ppm propylene is present in the purified gas stream after the $C_2/C_3$ splitter and almost all of this will appear with the recovered ethylene.

It is required that the recovered ethylene from the cracked gas feed stream meets standard specifications from the impurities standpoint. A tentative limit on impurities in the recovered ethylene was set as shown in the following Table II.

TABLE II

| | Tentative ACR Ethylene Specifications | |
|---|---|---|
| | | Specification Limits |
| 1. | Ethylene | 99.85 percent by volume, minimum |
| 2. | Methane plus ethane | 0.15 percent by volume, maximum |
| 3. | Carbon monoxide | 5 ppm by volume, maximum |
| 4. | Carbon dioxide | 10 ppm by volume, maximum |
| 5. | Acetylene | 10 ppm by volume, maximum |
| 6. | Sulfur | 5 ppm by weight, maximum |
| 7. | Water | 10 ppm by weight, maximum |

The ethylene recovered from the silver complexation process downstream of the stripper contains CO (30 ppm) and $CO_2$ (75 ppm) as a result of in situ $C_2H_4$ oxidation; $O_2$ (59 ppm) from $H_2O_2$ decomposition; and water vapor from the aqueous silver nitrate solution. The removal of CO and $O_2$ is simply effected by copper oxide and metallic Cu oxidation, respectively. For $H_2O$ removal, the use of molecular sieve and for $CO_2$ removal, caustic wash is employed to reduce their level appreciably below the specified limits.

Aqueous $AgNO_3$ solutions have been shown to be very stable. If a portion of the silver ion in solution is reduced to elemental silver, it can readily be redissolved in the presence of a small amount of $HNO_3$. Small amounts of $HNO_3$ in $AgNO_3$ solution also tend to provide added stability to the system especially in combination with $H_2O_2$.

The presence of hydrogen and perhaps other constituents of the feed gas have a reducing effect on silver ions which causes metallic silver precipitation from the solution. The metallic silver precipitate tends to filter out in the packing of the absorber and vent columns, thereby causing flooding earlier than expected. Metallic silver does not absorb ethylene. As the silver precipitates, the molarity of the silver nitrate solution drops which results in a net loss for ethylene loading in the solution.

The reduction of silver ions not only reduces the effectiveness of the silver solution in carrying out the ethylene separation but is also injurious to the solution circulating pump and other parts of the unit. This problem required development of some technique to inhibit the reduction and also to promote redissolution of silver in case it precipitates.

It was observed that hydrogen peroxide in a strong acidic medium diminishes the reduction effect of the reducing atmosphere. Since $H_2O_2$ decomposes in the process, a continuous feed is essential to maintain the stability of silver ions. Increasing the concentration of silver ions seems to enhance the reduction effect, thereby increasing the hydrogen peroxide consumption rate. A method of maintaining the silver ion-stability in 3 and 6 molar solutions with the help of $H_2O_2$ and nitric acid has been developed. As a result of such treatment, for every pound of hydrogen peroxide used, 500 and 200 pounds of ethylene can be separated by 3 and 6 molar silver nitrate solutions respectively without causing reduction of silver ions. A 0.5 to 1.0 N nitric acid concentration was maintained in the solution through the experimental period. Over extended duration of experimental runs, it has been observed that using 3 molar silver nitrate solution about 1000 lbs of ethylene can be separated for every pound of $H_2O_2$ consumed.

The net effect of $H_2O_2$ in the presence of $AgMnO_4$, since the solution medium is acidic, is reduction of $MnO_4^-$. The stoichiometric equation is as follows:

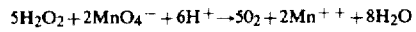

This equation indicates that almost all of the $H_2O_2$ in the side stream to be treated should be thermally destroyed before the $AgMnO_4$ is added. If any undercomposed $H_2O_2$ is present in the solution when the $MnO_4^-$ is added, more than the stoichiometric amount of $AgMnO_4$ based on $C_2^{--}$ content will be required.

If ethylene is not entirely removed from the $AgNO_3$ solution prior to the addition of $AgMnO_4$ it will be oxidized by $AgMnO_4$ according to the equation:

Therefore, to obtain the maximum benefit from the addition of $AgMnO_4$ for $C_2^{--}$ destruction, all $H_2O_2$ and $C_2H_4$ should be absent from the stream prior to $MnO_4^-$ addition.

Acetylide removal by oxidation may, alternatively, be effected by the addition of ozone or ozone-enriched air to the aqueous silver nitrate solution.

The removal of absorbed ethylene or propylene from the aqueous silver nitrate solution by desorption may be effected either by a swing cycling of the pressure on the aqueous solution or by treatment of the solution with an anti-solvent having a preferential ability to be absorbed in an aqueous nitrate solution. In pressure swing cycle desorption, there is effected a concurrent release of pressure on and an increase in the temperature of the solution stream (by provision of suitable compressors and heat exchangers), the pressure and temperature of the solution being subsequently returned to their initial levels before its recycle to the initial absorption step of the process. In anti-solvent desorption, the solution is treated with an anti-solvent such as an organonitrile, preferably acetonitrile, having preferred absorption characteristics greater than ethylene or propylene in such solution and thereby capable of displacing absorbed ethylene or propylene.

The process unit for carrying out the ethylene separation by metal complexing consisted of three main sections, namely: (a) absorption of ethylene from the feed gas mixture into silver nitrate solution, (b) stripping of the impurities absorbed into the solution along with the ethylene by purging pure ethylene through the solution and (c) desorption or strpping of ethylene from the silver nitrate solution in the stripper column.

A flow diagram of the process along with the preferred operating conditions is schematically shown in FIG. 1. As there shown, the feed gas is introduced through line 10 into the lower portion of absorber column 12 and the gas is absorbed and/or complexed in the aqueous silver nitrate solution. The resultant stream is successively passed through vent column 14, heat exchanger 16 and stripper column 18 to concurrently discharge ethylene product through heat exchanger 20 and treat the aqueous silver nitrate solution stream through a recycle path (comprising the parallel arrangement of heat exchanger 22 and acetylide removal chamber 24).

Figure 2:
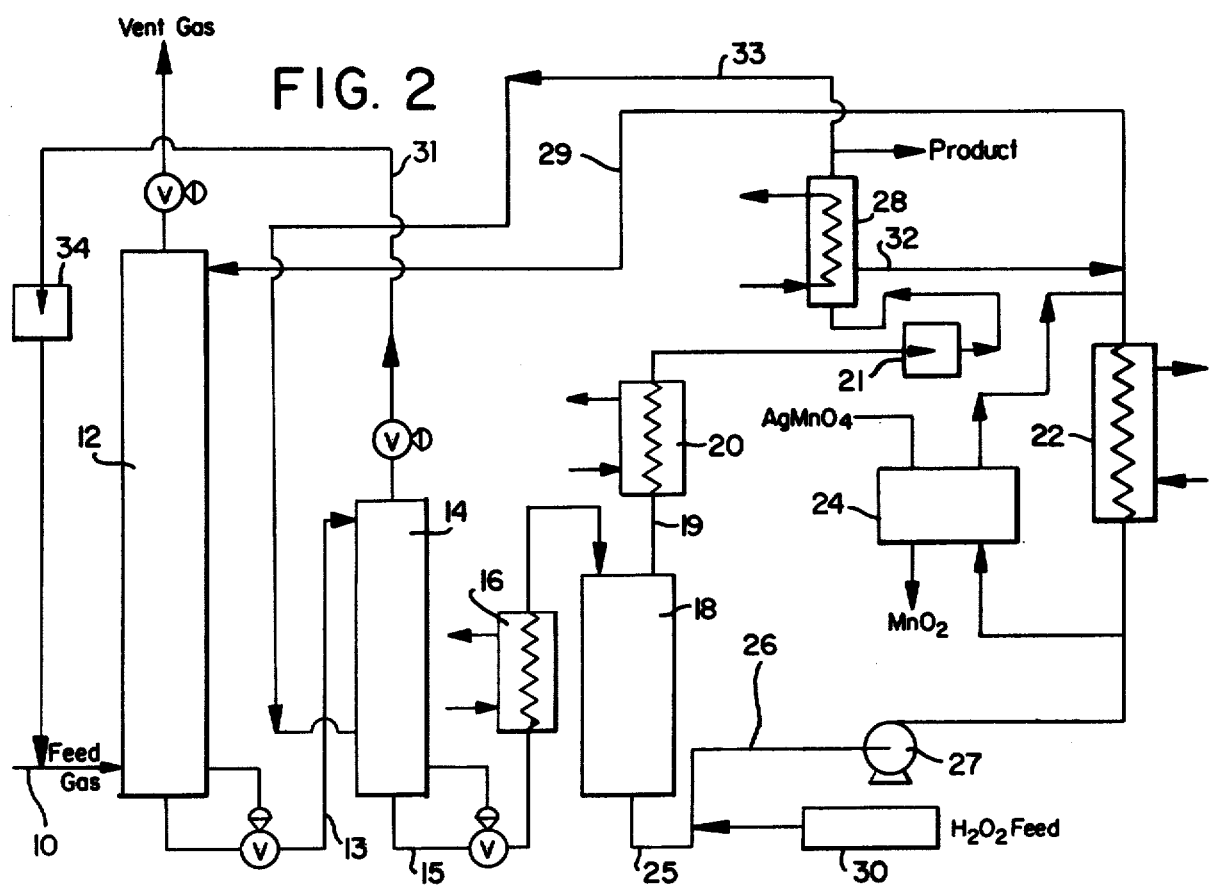
FIG. 2 is a more detailed schematic showing of a flow diagram of the process of the present invention indicating preferred operating conditions of the various parameters of each of the process steps.

A more detailed flow diagram of the process, along with an indication of a preferrec valving arrangement is shown schematically in FIG. 2 of the drawings. As there shown, the incoming feed gas stream employed may be one of a type discharged from an Advanced Cracking Reactor after passing through suitable quenching means, gasoline fractionation means, absorber means and stripper means for the removal of tar and other heavy fractions as well as the removal of carbon dioxide and hydrogen sulfide. Such a process is disclosed in the Hosoi and Keister article "Ethylene from Crude Oil" referred to hereinabove. The feed gas stream is then split into a $C_2$ fraction and a $C_3$ and higher hydrocarbon fraction. The analysis of components of the $C_2$ split fraction of the feed gas stream treated in the manner described is approximately as follows:

Ethylene—45.2 vol. %
Methane—17.46 vol. %
Carbon Monoxide—3.18 vol. %
Hydrogen—30.34 vol. %
Acetylene—Trace amounts
Propylene—Trace amounts In the manner similar to that described above with respect to flow diagram of FIG. 1 of the drawings, the split fraction feed gas stream is introduced through inlet line 10 to the lower portion of the absorber column 12 which is maintained at 35° C. and 295 psia. The column is externally cooled to the operating temperature and a gas vent is provided through suitable valving means at the upper end of the absorber column. The aqueous silver nitrate solution containing absorbed components of feed gas is taken from the lower portion of the absorber column through line 13 and introduced into the upper portion of vent column 14 which is maintained at 100 psia. The upper portion of vent column 14 permits the venting of additional gaseous components through suitable valve means. The aqueous silver nitrate solution is then passed from the lower end of vent column 14, through conduit 15 containing heat exchanger means 16, and introduced into the upper end of stripper column 18 which is maintained by external heating at 50° C. and at a pressure of 9 psia. the light gas fraction is taken off the top of stripper column 18 through line 19 and passes through heat exchanger 20 and compressor 21 to heat exchange coolor 28. There water is separated from the ethylene product and returned through line 32 to recycle in the system. The major portion of the ethylene (about 97%) is taken as product stream and a minor portion is recycled through line 33 to bubble through vent column 14 and assist in impurity removal.

The aqueous silver nitrate solution is taken off the bottom of the stripper column 18 and passes through line 25, recirculation pump means 27, heat exchanger 22 and return line 29 to the top of absorber column 12. Feed inlet means 30 is provided to introduce hydrogen peroxide into the recycled line 25 prior to passage through pump means 27.

The gas vented from column 14 passes through recycle line 31, is compressed in compressor means 34, and is fed into absorber column 12 with feed gas 10.

The conditions set forth in Table III present an example of the process of the invention applied to the production of ethylene from a purified, split stream of cracked hydrocarbon feedstock gas produced by the ACR process.

TABLE III

| Conditions | Feed Gas | Vent Gas | Product |
|---|---|---|---|
| Pressure, psia | 295 | 295 | 300 |
| Temp. | 40° C. | 40° C. | 35° C. |
| Rate, M lb/hr | 179.1 | | |
| Mol. Wt. | 18.13 | | |
| Stream (drawing No. FIG. 2) | No. 10 | No. 31 | No. 32 |
| Components/Rate | M lb/hr | M lb/hr | M lb/hr |
| Hydrogen | 6.042 | 6.042 | 0.0 |
| Nitrogen | 1.095 | 1.095 | 0.0 |
| Carbon Monoxide | 8.804 | 8.80 | 0.004 |
| Carbon Dioxide | — | — | 0.009 |
| Methane | 27.665 | 27.66 | 0.005 |
| Acetylene | 0.000116 | 0.0 | 0.0 |
| Ethylene | 125.250 | 1.88 | 123.37 |
| Ethane | 9.833 | 9.823 | 0.010 |
| Propylene | 0.409 | 0.006 | 0.403 |
| Oxygen | — | — | 0.045 |
| Water | — | 0.025 | 0.026 |

Comments on FIG. 2
Recycle (vent column No. 14) stream (No. 33) has the same composition as product stream (No. 32) but is only 10% of the product stream. $H_2O_2$ feed is 123.0 lbs/hr (contained $H_2O_2$ in 30% solution).

Another aspect of the present invention consists of an arrangement for minimizing energy consumption in a process for the recovery of ethylene from mixed gases by a selective, reversible reaction with silver nitrate. In the flow diagrams of FIGS. 3 and 4, stream P-1 represents the mixed gas stream containing ethylene and other gases which is fed to Tower A where it is contacted with an aqueous solution of silver nitrate (stream P-2). The reaction between ethylene and silver nitrate results in a soluble complex which passes out of Tower A in stream P-4. The remaining gases, essentially ethylene-free, leave Tower A in stream P-4. As a normal result of the release of heat of reaction between ethylene and silver nitrate as well as heat of solution and heat mixing, the temperature of stream P-4 will be as much as 15 to 20 degrees C. higher than the temperature of stream P-2 if Heat Exchanger D (FIG. 3) is not used. This higher temperature tends to reverse the desired reaction and increase the circulation rate required for stream P-2.

Stream P-4 is expanded to a lower pressure through valve V-1, partially reversing the reaction and releasing ethylene from the solution with a resultant lowering of temperature. Although a sufficiently low pressure could be used to remove essentially all the ethylene, experience has shown that such a low pressure would be economically undesirable. The recovered ethylene will normally have to be compressed to make it available to subsequent users, and the use of extremely low pressures raises compression costs inordinately. Therefore, it is preferable to operate Tower B at a more reasonable pressure and raise the solution temperature to accomplish recovery of the ethylene.

It is normal to heat stream P-5 by exchange with stream P-9 in Exchanger C and add additional heat in Exchanger E, which is the reboiler associated with Tower B. By so doing, the solution temperature is raised sufficiently that the recovered ethylene leaves Tower B in stream P-7, and the regenerated solution leaves in stream P-8 and is pumped back to Tower A through Exchanger C by pump P-1.

Figure 3:
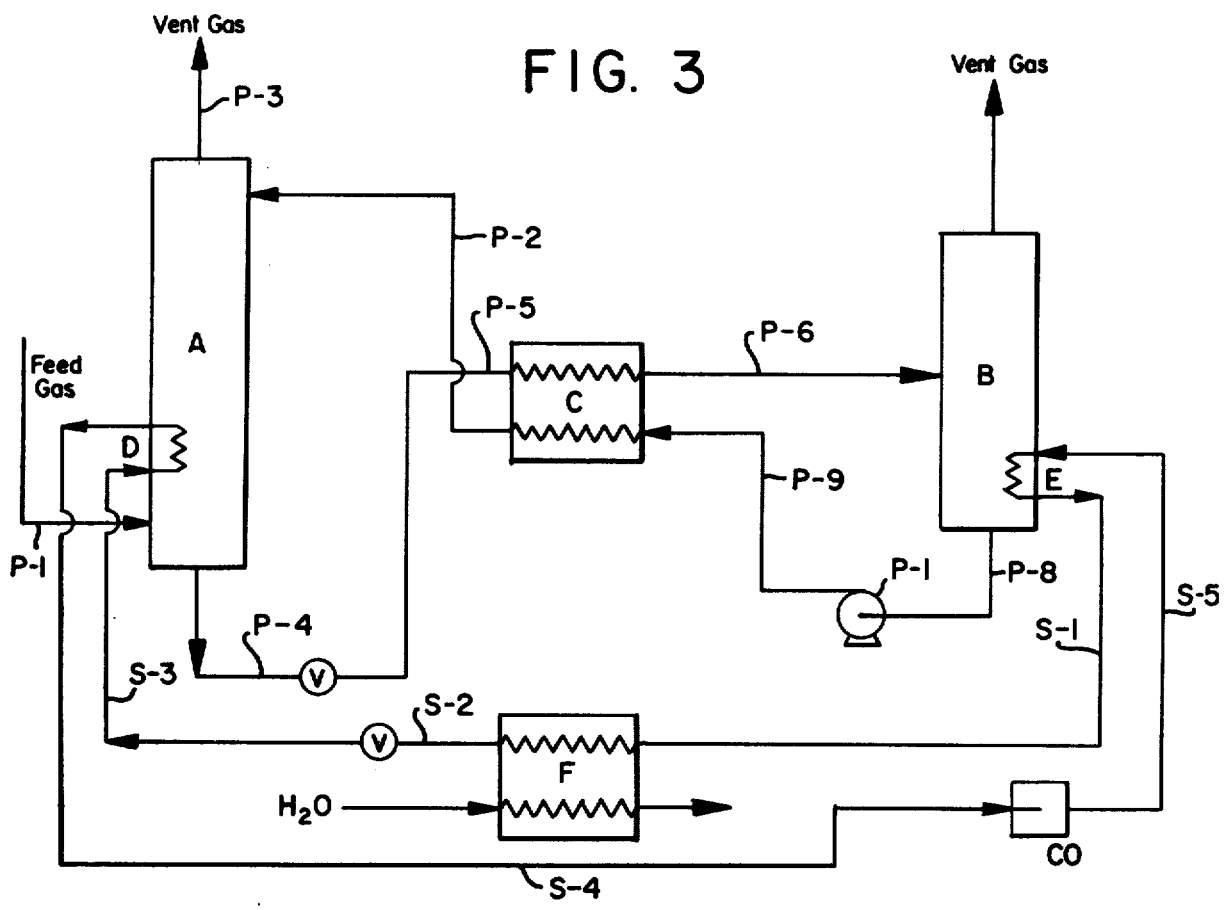
FIG. 3 is a schematic flow diagram of the heat cycle for energy utilization in a process for ethylene recovery by silver salt implementing the sound practices of the art.
Figure 4:
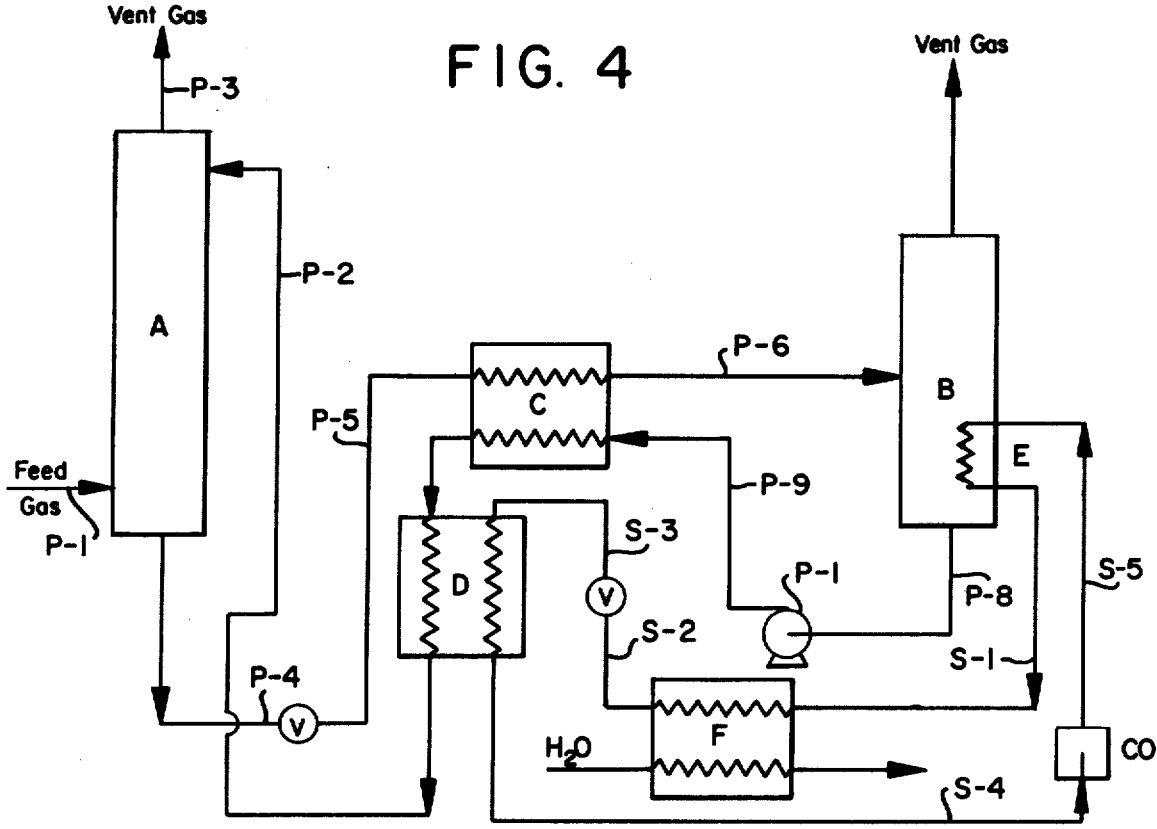
FIG. 4 is a schematic flow of one aspect of the present invention, wherein an improved heat cycle concept is employed to provide improved energy utilization.

Normal practice would implement Exchangers D and E as separate, unconnected, devices with an external cooling medium used on Exchanger D and an external heating medium used on Exchanger E as employed in FIG. 3. The specific nature of this process improvement over such normal practice is the coupling of Exchangers D and E by the circulation of a working fluid which is evaporated in Exchanger D, providing cooling at that point and is then compressed by compressor CO and condensed in Exchanger E where heat is released, as is shown in FIG. 4 of the drawings.

A large number of materials can be used as the working fluid, one of them being a fluorocarbon refrigerant fluid such as UCON 216. With this material as the working fluid, typical operating conditions might be a liquid at 70° C. and 42 psia for stream S-1. Stream S-1 would preferably be cooled to approximately 40° C. in Exchanger F by use of cooling water, or other available streams and the resulting stream S-2 would then be expanded into Exchanger D through Valve U-2. Stream S-3, at a pressure of 12 psi, would be evaporated at a temperature of 30° C., and the resulting stream S-4 would then go to compressor C-1 and be compressed to 40 psia. Stream S-5, leaving the compressor, would then proceed to Exchanger E where it would be condensed at 70° C.

With the above conditions of operation, it would be possible to cool stream P-4 (stream P-2 in FIG. 4) to any temperature higher than 30° C. and to heat stream P-8 to any temperature below 70° C., dependent on the amount of area provided in Exchangers D and E. Under operating rates such that the heat loads in Exchangers D and E are both 29.5 MM Btu/hr, Exchanger F has a heat duty of 6.8 MM Btu/hr, and the heat equivalent of the energy necessary to drive compressor C-0 is 13.4 MM Btu/hr. The net savings through the application of this aspect of the invention for the above conditions is 22.7 MM Btu/hr of cooling load and 16.2 MM Btu/hr of heating load.

Obviously, the operating conditions for the working fluid, and the selection of working fluid, can be changed to obtain variation of the sink temperature at Exchanger D of the source temperature at Exchanger E.

What is claimed is:

1. The process for the separation of ethylene or propylene from a purified, multi-component gas stream produced from the thermal cracking of hydrocarbons and containing ethylene or propylene and other low molecular weight components comprising the steps of:
   (a) introducing, said multi-component gas stream into an aqueous silver salt solution stream to effect the absorption and/or complexing of the contained ethylene or propylene and reaction of trace acetylenes with the silver metal ions of such solution;
   (b) venting of the silver salt solution stream at reduced pressure to remove the dissolved other low molecular weight components;
   (c) treating the resulting silver salt solution stream to separate the absorbed and/or complexed ethylene or propylene from the silver salt stream;
   (d) further treating the resultant silver salt solution stream to release the contained trace acetylenes therefrom and provide an aqueous silver salt stream; and
   (e) recycling said aqueous silver salt stream to said introducing step.

2. The process in accordance with claim 1, wherein said treating to separate said absorbed ethylene or propylene from said silver salt stream is effected by the addition of anti-solvent to said stream.

3. The process in accordance with claim 1, wherein said treating to separate said absorbed ethylene or propylene from said silver salt stream is effected by the concurrent release of pressure on and the increase in temperature of the stream, the pressure and temperature subsequently being returned to their initial levels prior to recycle of the stream to said introducing step.

4. The process in accordance with claim 1, wherein said aqueous silver salt solution stream is a nitrate stream containing absorbed and/or complexed ethylene or propylene and trace acetylenes is stabilized by the addition of hydrogen peroxide and the nitrate level is maintained by the addition of nitric acid.

5. The process in accordance with claim 1, wherein said further treating step comprises the release of trace acetylenes by treatment with silver permanganate.

6. The process in accordance with claim 1, wherein said further treating step comprises the release of trace acetylenes by treatment with ozone or ozone-enriched air.

7. The process in accordance with claim 1, wherein said aqueous silver salt solution is an aqueous solution of silver nitrate.

8. Process in accordance with claim 2, wherein said anti-solvent added to said stream comprises an organonitrile.

9. The process in accordance with claim 8, wherein said organonitrile is acetonitrile.

* * * * *